United States Patent [19]

Dalton et al.

[11] Patent Number: 5,571,443
[45] Date of Patent: Nov. 5, 1996

[54] SYNERGISTIC COMBINATION OF 2-(THIOCYANOMETHYLTHIO)BENZOTHIA- ZOLE AND THIOPHANATE COMPOUNDS USEFUL AS FUNGICIDES

[75] Inventors: Dennis L. Dalton, Singapore; Robert A. Oppermann, Montville, N.J.; Hayley Chambers, Loyang Valley, Singapore

[73] Assignee: Buckman Laboratories International, Inc., Memphis, Tenn.

[21] Appl. No.: 366,907

[22] Filed: Dec. 30, 1994

[51] Int. Cl.$^6$ ............................... C14C 9/00; C14C 9/02
[52] U.S. Cl. .................. 252/8.57; 8/94.19 R; 8/94.2; 8/94.21; 8/94.22; 8/94.27; 8/94.32; 8/94.33
[58] Field of Search ............... 252/8.57; 514/367; 8/94.19 R, 94.2, 94.21, 94.22, 94.27, 94.32, 94.33; 427/389

[56] References Cited

U.S. PATENT DOCUMENTS

| | | | |
|---|---|---|---|
| 3,463,785 | 8/1969 | Buckman et al. | 548/169 |
| 3,929,448 | 12/1975 | Brantley | 504/115 |
| 4,028,464 | 6/1977 | Bell | 514/388 |
| 4,293,559 | 10/1981 | Buckman et al. | 514/367 |
| 4,479,961 | 10/1984 | Martin | 514/367 |
| 4,595,691 | 6/1986 | Lamarre et al. | 514/367 |
| 4,605,668 | 8/1986 | Takahashi et al. | 514/485 |
| 4,752,615 | 6/1988 | Takahashi et al. | 514/479 |
| 4,839,373 | 6/1989 | Ito et al. | 514/367 |
| 4,866,081 | 9/1989 | Ito et al. | 514/367 |
| 4,944,892 | 7/1990 | Leathers et al. | 252/92 |
| 5,129,946 | 7/1992 | Evans | 106/18.3 |

FOREIGN PATENT DOCUMENTS

55/76806 6/1980 Japan.

OTHER PUBLICATIONS

Derwent Abstract of Australian Patent AU 8546819 (Apr. 10, 1986).
Translation of Japanese Patent Application No. 55/76806 (Jun. 10, 1980).

Primary Examiner—Anthony Green
Attorney, Agent, or Firm—Finnegan, Henderson, Farabow, Garrett & Dunner, L.L.P.

[57] ABSTRACT

A method for preventing the deterioration of leather by controlling the growth of fungus, wherein the leather is contacted with TCMTB and a thiophanate compound present in a combined amount synergistically effective to control the growth of at least one fungus.

20 Claims, 2 Drawing Sheets

SYNERGISTIC COMBINATION OF 2-(THIOCYANOMETHYLTHIO)BENZOTHIAZOLE AND THIOPHANATE COMPOUNDS USEFUL AS FUNGICIDES

BACKGROUND OF THE INVENTION

1. Field of the Invention

The present invention relates to new uses of synergistic fungicidal combinations of 2-(thiocyanomethylthio)benzothiazole (TCMTB) and a thiophanate compound to control fungal growth on a variety of substrates and in aqueous systems.

2. Description of the Related Art

Fungi, also referred to as molds, rusts, mildews, smuts, etc., are multicellular organisms that are typified by a branching cellular structure. Fungi develop from microscopic spores, which are omnipresent in nature (in soil, water and air), to macroscopic structures that grow on almost any substance which offers a source of moisture and some form of nutrients.

Because fungi are widely present throughout the environment, they are also found in various industrial operations where they can cause economic damage resulting from their growth on industrial raw materials and goods. Fungal growth can cause deterioration, i.e., discoloration or actual degradation of the material or good, thereby reducing its economic value.

An example of an industry where fungal growth may dramatically reduce the value of the end product is the leather industry. Different species of fungi, such as molds, are encountered at various stages in the processing of leather. For instance, the pickling stage, wherein the hides are transformed into an acid environment for tanning, even strong pickle solutions are subject to attack by some microorganisms. Fungi, molds in particular, may be troublesome and cause discoloration of the pickled stock, especially if the stock is held for a period of time before tanning, Finally, the moisture, pH, and temperature characteristics of the tanning process create almost ideal conditions for the growth of a variety of fungi, including *Aspergillus, Penicillium* and *Paecilomyces*, which may discolor and permanently downgrade the economic value of finished leather.

Other industries where fungal growth is also a problem include: the lumber industry: mold growth on wooden substrates, so-called sapstaining and decay of untreated lumber, particle board and other wooden products; the papermaking industry: fungal growth on cellulose pulp; fungal slime in paper mill systems; the textile industry: mold growth and its resulting staining and decay of textile fabrics; the agricultural industry: mold and other fungal growth on seeds, plants, and crops; and the coating industry: fungal attack on glues and surface coatings. Common fungal species that grow on these types of materials include *Aspergillus, Penicillium* and *Paecilomyces*.

In addition to solid substrates, aqueous systems containing organic materials are also subject to microbiological attack and degradation. Microorganisms may grow, for example, in aqueous systems such as latexes, metal working fluids, cooling water, aqueous emulsions, aqueous detergents, and resins formulated in aqueous solutions, emulsions, or suspensions. Such products frequently contain relatively large amounts of water. The temperature at which these products are stored as well as their pH makes these products susceptible to the growth of fungi.

Fungal degradation of such aqueous systems containing organic material may manifest itself in a variety of problems, including loss of viscosity, gas formation, objectionable odors, decreased pH, emulsion breaking, color change, and gelling. Additionally, fungal deterioration of aqueous systems can also cause fouling of the related water-handling system, which may include cooling towers, pumps, heat exchangers, and pipelines, heating systems, scrubbing systems, and other similar systems.

Various chemicals, generally known as industrial fungicides, have been used to prevent this fungal deterioration of industrial and raw materials and goods. For instance, 2-(Thiocyanomethylthio)benzothiazole (TCMTB) is one effective industrial fungitide. The use of TCMTB as an industrial fungicide has been described in U.S. Pat. Nos. 4,293,559, 4,866,081, 4,595,691, 4,944,892, 4,839,373, and 4,479,961. TCMTB is manufactured by Buckman Laboratories International, Inc., and sold as Busan® 30WB, Busan® 1030, Busan® 1118 and other products.

Another example of an industrial fungicide is thiophanatemethyl (TPM). TPM is also known as 4,4'-o-phenylenebis[3-thioallophanate], as dimethyl [(1,2-phenylene) bis(iminocarbonothioyl)]biscarbamate, and cerocobin-m. TPM is used as a fungicid® in agricultural applications, such as seed treatment to protect against fungal growth on the seeds. TPM is manufactured by Nippon Soda Co., Ltd., Japan, and sold as the product Topsin-M.

Despite the existence of such fungicides, there remains a need for cost-effective technology that performs in a particular system and offers equal or better protection at lower cost and lower concentrations of fungicide. When used, the concentration of fungicides and the corresponding treatment costs for such use, can be relatively high. Important factors in the search for cost-effective fungicides include efficacy in the particular industrial application, the duration of fungicidal effect, the ease of use, and the effectiveness of the fungicide per unit weight.

SUMMARY OF THE INVENTION

In view of the industry's search for more cost effective fungicides, the present invention offers an improved fungicide and, accordingly, presents a solution for a number of major industries where fungi are a problem.

Accordingly, one embodiment of the invention provides a method for protecting leather during a leather tanning process. In this process, the leather to be tanned is contacted with TCMTB and a thiophanate compound in a combined amount synergistically effective to control the growth of at least one fungus on the leather.

Another related embodiment of the invention provides a liquor used in a leather-tanning process. The liquor comprises TCMTB and a thiophanate compound where these two ingredients are present in a combined amount synergistically effective to control the growth of at least one fungus on the leather to be tanned.

Another embodiment of the invention provides a method for controlling the growth of at least one fungus on a textile substrate in a textile manufacturing process. The textile substrate is contacted with TCMTB and a thiophanate compound in a combined amount synergistically effective to control the growth of at least one fungus.

Yet another embodiment of the present invention relates to a dip bath used in a textile manufacturing process. The dip bath of the present invention comprises TCMTB and a thiophanate compound in a combined amount synergistically effective to control the growth of at least one fungus on a textile material.

A further embodiment of the present invention relates to a method for protecting lumber from fungal deterioration. The lumber is contacted with TCMTB and a thiophanate compound in a combined amount synergistically effective to control the growth of at least one fungus on the lumber.

Related to the method for protecting lumber, another embodiment of the present invention relates to a dip bath used in a lumber process. The dip bath of the present invention comprises TCMTB and a thiophanate compound in a combined amount synergistically effective to control the growth of at least one fungus on the lumber.

The present invention is also drawn to a method for preventing fungal deterioration of an aqueous system capable of supporting the growth of a fungus wherein the aqueous system is treated with TCMTB and a thiophanate compound in a combined amount synergistically effective to control the growth of at least one fungus.

The methods of the invention result in improved fungicidal effectiveness at lower concentrations and at lower cost than the application of either TCMTB or thiophanate compounds individually. The synergistic combination of TCMTB with a thiophanate compound achieves superior fungicidal activity at lower concentrations than either fungicide alone against typical fungal organisms that grow on and cause deterioration of industrial materials such as leather, lumber, including particle board and plywood, textiles, and of aqueous solutions, suspensions, or emulsions.

The foregoing and other features and advantages of the present invention will be made more apparent from the following description of the preferred embodiments.

DESCRIPTION OF THE PREFERRED EMBODIMENTS

Figure 1:
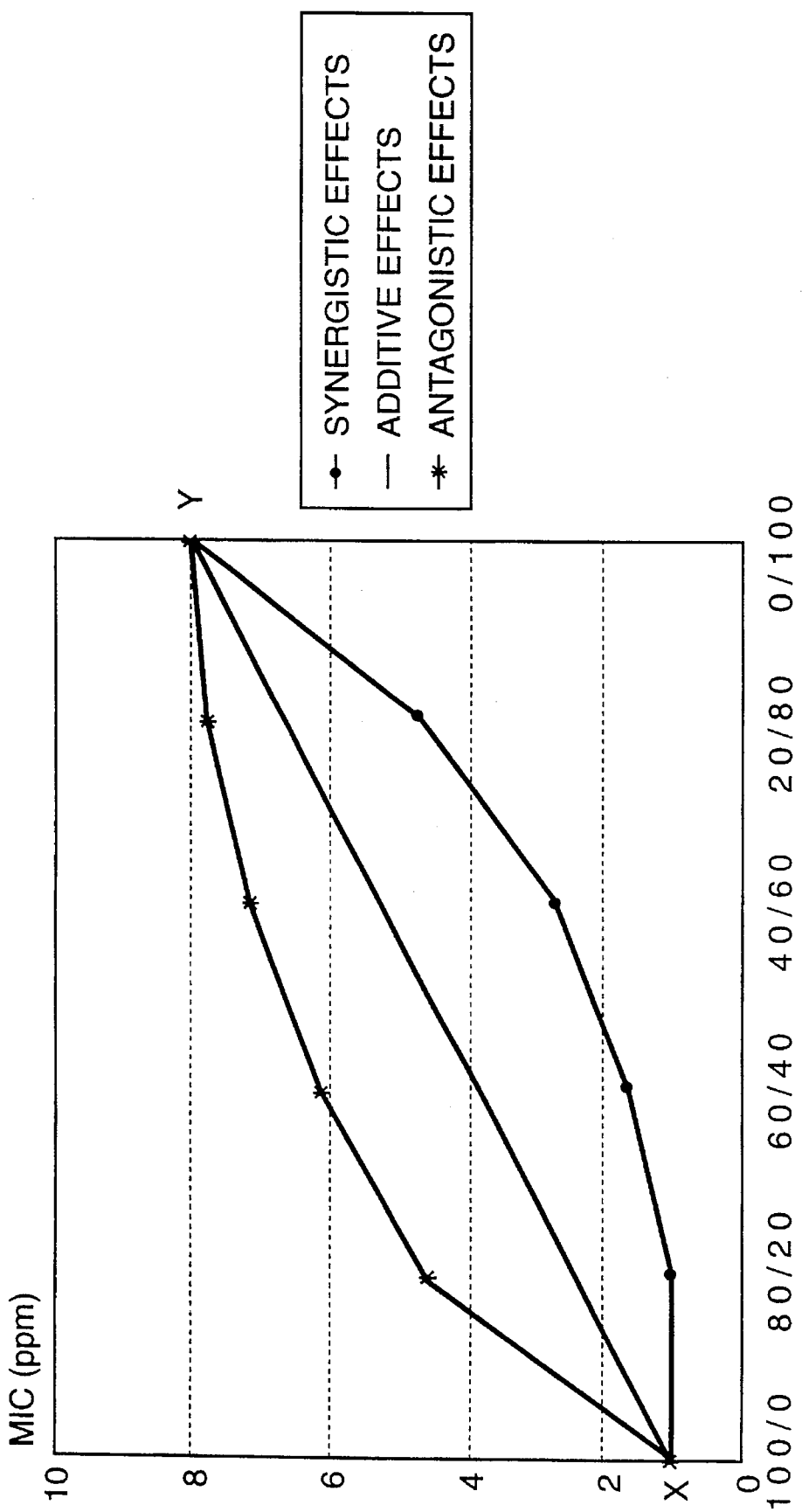
FIG. 1 shows the standard evaluation of synergistic effects as commonly used in the literature. The minimum inhibitory concentration (MIC), as determined using the binary dilution method, is plotted against the respective microbicide mixture ratio.

Reference will now be made in detail to the present preferred embodiments of the invention.

According to the invention, the synergistic combination of TCMTB with a thiophanate compound achieves superior fungicidal activity at lower concentrations than either fungicide alone. The methods of the invention result in improved fungicidal activity at lower concentrations and at lower cost than the application of either TCMTB or thiophanate compounds individually. As described below, the synergistic combination of TCMTB and a thiophanate compound are fungicidally effective against typical fungi that grow on and cause deterioration of industrial materials such as leather, lumber, including particle board and plywood, textiles, and of aqueous systems.

According to the present invention, control of fungal growth means that the fungal growth on a substrate is reduced to desired levels, and/or fungal growth on the substrate is maintained at or below desired levels for substrate preservation. The methods of the invention employing a synergistic combination of TCMTB and a thiophanate compound can in many cases even reduce the total fungal count to undetectable limits and maintain it at that level for a significant period of time.

The methods of the invention employ the synergistic fungicidal effect between TCMTB and a thiophanate compound to control fungal growth in a variety of industrial systems. That is, the combination of TCMTB and a thiophanate compound achieves superior fungicidal activity at lower concentrations to control the growth of fungal organisms as compared to the fungicidal capability of the same amount of either TCMTB and a thiophanate compound individually. This superior synergistic effect presents a distinct economic advantage and increases the fungicide's effectiveness per unit weight. When used in a method of the invention, the TCMTB and the thiophanate compound may be added separately or together in a single formulation. Each of these methods will be further discussed below.

The thiophanate compounds useful in the invention include compounds of the formula:

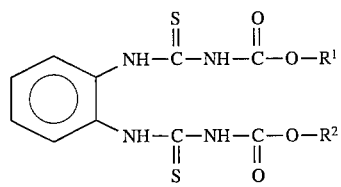

$R^1$ and $R^2$ are the same or different and are a $C_1$–$C_6$ alkyl group, preferably ethyl or methyl, most preferably methyl. Particularly preferred is the dimethyl ester or TPM. TCMTB is discussed above.

The present invention provides a method for protecting leather during a leather tanning process comprising the step of contacting the leather to he tanned with TCMTB and a thiophanate compound. The TCMTB and the thiophanate compound are present in a combined amount synergistically effective to control the growth of at least one fungus on the leather. The TCMTB and the thiophanate compound may be used in the tanning process in the similar amounts and manner as other fungicides. This, to some extent, will depend on the degree of fungal resistance required and may be readily determined by one skilled in the art. Depending on raw materials and processing conditions, protection from fungal attack will be obtained within the general range of 0,075%–0,200% of white stock weight using the inventive synergistic combination of TCMTB and a thiophanate compound. Higher dosages will enhance results.

A typical leather tanning process comprises a number of stages, including, but not limited to, a pickling stage, a chrome-tanning stage, a vegetable-tanning stage, a post-tan washing stage, and a fatliquoring stage. In each stage, the synergistic combination of TCMTB and the thiophanate compound may be a component of the appropriate tanning liquor applied to the leather undergoing tanning. Incorporating the TCMTB and the thiophanate compound in the tanning liquor protects the leather from fungal deterioration.

The TCMTB and thiophanate compound may be used during all processing stages in the leather tanning process not or only those stages where the fungal problem is occurring. Preferably, the TCMTB and the thiophanate compound combination is uniformly dispersed under agitation into the relevant liquor depending on the process to which it will be added, e.g., the pickling liquor. This method of application ensures that the invention is applied on to the hides or leather in such a manner so as to result in the desired protection of the hides or leather against fungal attack and degradation.

Typical tanning liquors include, for example, a pickling liquor, a chrome-tanning liquor, a vegetable-tanning liquor, a post-tan washing liquor, and a fatliquor. The present invention is, therefore, also drawn to a tanning liquor used in a leather-tanning process. The liquor comprises TCMTB and a thiophanate compound present in a combined amount synergistically effective to control the growth of at least one fungus on the leather to be tanned.

The present invention also provides a method for controlling the growth of at least one fungus on a textile substrate in a textile manufacturing process. The method comprises contacting the textile substrate with TCMTB and a thiophanate compound present in a combined amount synergistically effective to control the growth of at least one fungus. The TCMTB and the thiophanate compound may be used in the textile process in the similar amounts and manner as other fungicides. This, to some extent, will depend on the material to be treated and the degree of fungal resistance required. This may be readily determined by one skilled in the art. Depending on the degree of preservation required and processing conditions, protection from fungal attack will be obtained within the general range of 1.00–3.00% based on fabric weight using the inventive synergistic combination of TCMTB and a thiophanate compound. Preferably, the contacting step comprises dipping the textile substrate in a bath containing the TCMTB and the thiophanate compound.

The present invention is also drawn to a dip bath used in a textile manufacturing process comprising TCMTB and a thiophanate compound present in a combined amount synergistically effective to control the growth of at least one fungus on a textile material.

The present invention additionally provides a method for protecting lumber from fungal deterioration comprising the step of contacting the lumber with TCMTB and a thiophanate compound. The TCMTB and the thiophanate compound are present in a combined amount synergistically effective to control the growth of at least one fungus on the lumber. The contacting step is accomplished by spraying the lumber with an aqueous dispersion of the TCMTB and the thiophanate compound or dipping the lumber into a bath containing the TCMTB and the thiophanate compound.

Preferably, the step of contacting the lumber comprises dipping the lumber into a bath containing the synergistic combination of TCMTB and the thiophanate compound. The TCMTB and the thiophanate compound are preferably uniformly dispersed in an aqueous bath (for example, by agitation) prior to the dipping of the lumber into the bath. In general, the lumber is dipped into the bath, raised, allowed to drip dry, and then air dried. The dip time will depend, as is known in the art, on a variety of factors such as the moisture content of the lumber, type and density of the wood, etc.

The present invention is also drawn to a dip bath used to protect lumber from fungal deterioration comprising TCMTB and a thiophanate compound. The TCMTB and the thiophanate compound are present in a combined amount synergistically effective to control the growth of at least one fungus on the lumber. The TCMTB and the thiophanate compound may be used to protect the lumber in similar amounts and manner as other fungicides. This, to some extent, will depend on the degree of fungal resistance required and may be readily determined by one skilled in the art. Depending on the types of wood and components in the treating solution, protection from fungal attack will be obtained within the general range of 0.70–4.50 % by weight of the treated solution using the inventive synergistic combination of TCMTB and a thiophanate compound.

Yet another aspect of the present invention is a method for preventing fungal deterioration of an aqueous system capable of supporting the growth of a fungus. The aqueous system is treated with TCMTB and a thiophanate compound present in a combined amount synergistically effective to control the growth of at least one fungus. The aqueous system may be selected from a latex, a metal working fluid, an aqueous emulsion, an aqueous detergent, and an aqueous resin formulation.

Another embodiment of the present invention is a method for preventing fungal deterioration of paper or of pulp, particularly in a papermaking process. The paper or pulp is contacted with TCMTB and a thiophanate compound present in a combined amount synergistically effective to control the growth of at least one fungus.

In a process of the invention, wet-lap pulp is contacted with the synergistic combination of TCMTB and a thiophanate compound by spraying an aqueous dispersion of the present invention onto the pulp after the pulp leaves the presses. Alternatively, the pulp can be contacted by mixing the TCMTB and the thiophanate compound into the pulp/white water mixture prior to pulp reaching the formation wire.

When treating paper and paperboard, the TCMTB and the thiophanate compound can be applied into the white water system for incorporation into the body of the paper or paperboard. Alternatively, as with other known fungicides, the TCMTB and the thiophanate compound can be mixed into a coating used to coat the finished paper or paperboard.

Depending on the application, the fungicidal composition used in the methods of the present invention may be prepared in various forms known in the art. It may be prepared in liquid form as an emulsion or as a solution by dissolving the TCMTB and the thiophanate compound in a solvent or combination of solvents. Suitable solvents include, but are not limited to, monochlorobenzene, cyclohexanone, tetrahydrofuran, diethylene glycol monomethyl ether, etc. The fungicidal composition can be prepared as a concentrate for dilution prior to its intended use.

When prepared as an aqueous composition, a surfactant may be added to obtain a formulation that will emulsify in the aqueous system or in water. An emulsion in water can be prepared by adding a surfactant and emulsifying the composition in water. Preferably, the surfactant is a nonionic surfactant, such as, for example, polyoxypropylene alkyl phenol ether, polyoxyethylenepolyoxypropylene block copolymer, polyoxyethylene alkyl ether, and polyoxyethylene fatty acid ester.

The composition of the present invention can also be prepared in powder form. In a preferred method of preparation, TCMTB, which is commercially available as a technical liquid product, is deposited on a carrier such as diatomaceous earth or kaolin and mixed with TPM in the form of a technical powder. A surfactant may be added to the powder mixture to prepare a wettable powder that will disperse in water and aqueous systems. Preferably, the surfactant is nonionic. More preferably, the nonionic surfactant is polyoxypropylene alkyl phenol ether, polyoxyethylene-polyoxypropylene block copolymer, polyoxyethylene alkyl ether, or polyoxyethylene fatty acid ester. The composition of the present invention can additionally be prepared as a paste by dissolving it in an organic solvent and adding a surfactant.

The TCMTB and the thiophanate compound may be used together as a single formulation and added to a system or applied to a substrate. Alternatively, the TCMTB and the thiophanate compound may be added to a system or applied to a substrate as separate components such that the combined amount is synergistically effective to control the growth of a least one fungi. In a preferred embodiment, the synergistic combinations of TCMTB and a thiophanate compound are those combinations having a weight ratio of the TCMTB to the thiophanate compound between 99:1 and 1:99, more preferably between 60:40 and 20:80, and most preferably, between 50:50 and 30:70. The ratio may vary depending on the intended use, the fungus, and the material or product to which it is applied.

The method using the compositions described above has been shown to have synergistic activity as confirmed using standard laboratory techniques as illustrated below. The following examples are intended to illustrate, not limit, the present invention.

EXAMPLE 1

Fungicidal Activity of TCMTB and TPM

The synergistic effects of the combined use of TCMTB and TPM against fungus were measured by the binary dilution method. The two components, in solid form, were dissolved in methylcarbitol or acetone. Solutions were prepared having concentrations ranging from 0.01 to 1% by weight of TCMTB or TPM. Each solution was then added, in an appropriate amount to achieve concentrations of 0.1, 0.5, 1.0, 2.0, 4.0, 8.0 ppm etc., of TCMTB or TPM in 10 ml aliquots of sterilized nutrient broth in minimum inhibitory concentration (MIC) test tubes, i.e., 10 ml tubes made from borosilicate glass and having plastic screw-on caps.

After agitation, 0.1 ml of a spore suspension containing a mixture of at least three types of fungi, identified as *Penicillium*, *Aspergillus niger*, and *Aspergillus ninulans*, was added to each tube as inoculum. The mixture had been isolated and cultured from molded chrome-tanned leather samples and contain at least these three fungi. The test tubes were agitated to ensure proper mixing of the fungal spores into the nutrient broth. The tubes were then incubated at 32° C. for 7 days. The lowest concentration of each fungicide or fungicide combination that prevented growth of the fungi in the broth, i.e., the minimum inhibitory concentration (MIC), was taken as the endpoint and is shown in Table 1 below.

As shown in Table 1, 2.0 ppm of TCMTB alone and higher concentrations showed no growth, while concentrations below 2.0 ppm did show growth. Thus, the Minimum Inhibitory Concentration (MIC) of TCMTB (100%) is 2.0 ppm. Where Table 1 shows 80% TCMTB and 20% TPM with a corresponding MIC of 1.1 ppm, this means that 1.1 ppm of an 80/20 combination of TCMTB/TPM provided control.

FIG. 1 shows evaluation standards for synergistic effects as commonly used in the literature. The minimum inhibitory concentration (MIC), determined using the binary dilution method, is plotted against the respective mixture ratios of the microbicide. If the plotted MIC's form a straight line connecting points X and Y, the microbicidal effect is only additive. An additive effect means that the performance of the combined components is the same as the sum of the performance of each of the components used individually. If the plotted MIC's form a curve above the additive line, the microbicidal effect is antagonistic, meaning the two components counteract each other. The performance of the combined components is poorer than each used individually. However, if the plotted MIC's form a curve under the additive line, the microbicidal effects are synergistic. When a synergistic effect is achieved, the performance of the combined components is greater than the sum of the performance of the individual components.

Figure 2:
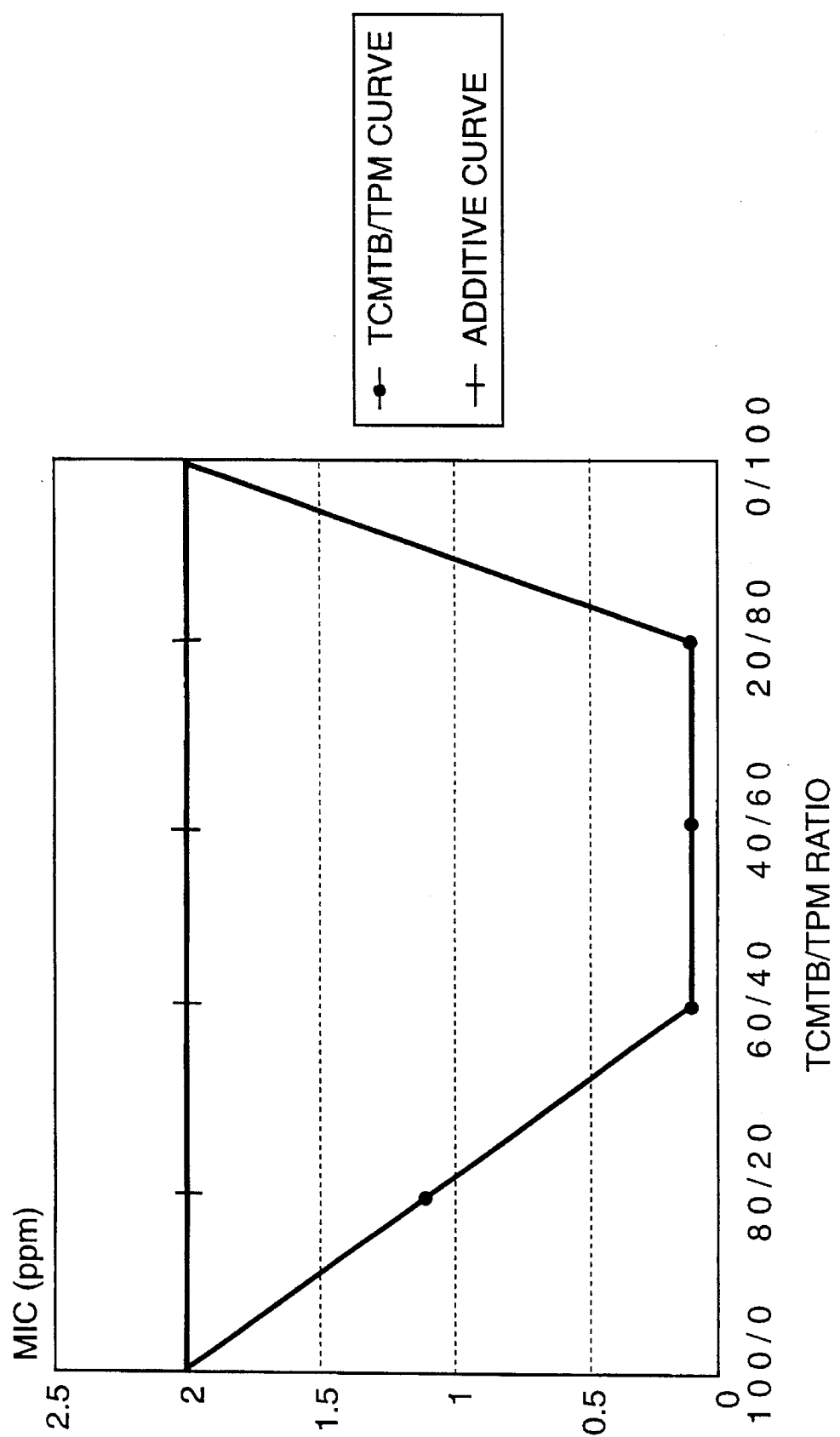
FIG. 2 sets forth the MIC's for various mixtures of TCMTB and TPM as determined against a mixture of fungi.

Table 1 below shows the MIC's for TCMTB, TPM and the various mixtures determined according to this technique. FIG. 2 shows these same MIC values in graphic form against the mixture of fungi described above. FIG. 2 also shows that TCMTB/TPM combinations are clearly synergistic in their microbicidal performance against the mixture of fungi used in this study. As can be seen from the curve, the strongest synergistic properties were exhibited at TCMTB/TPM ratios between 60/40 and 20/80.

TABLE 1

Minimum Inhibitory Concentrations (MIC) for TCMTB, TPM and TCMTB/TPM combinations against a mixture of fungal species isolated from molded chrome-tanned leather.

| % TCMTB | % TPM | MIC (ppm) |
| --- | --- | --- |
| 100 | 0 | 2.0 |
| 80 | 20 | 1.1 |
| 60 | 40 | 0.1 |
| 40 | 60 | 0.1 |
| 20 | 80 | 0.1 |
| 0 | 100 | 2.0 |

What is claimed is:

1. A leather-tanning liquor composition comprising
(a) 2-(thiocyanomethylthio)benzothiazole and
(b) a thiophanate compound wherein (a) and (b) are present in a combined amount synergistically effective to control growth of at least one fungus on leather to be tanned, wherein the leather-tanning liquor composition is a pickling liquor; a chrome-tanning liquor, a vegetable-tanning liquor, a post-tan washing liquor, or a fatliquor.

2. The composition of claim 1, wherein the thiophanate compound is thiophanate-methyl.

3. The composition of claim 1, wherein said composition is a pickling liquor to be applied to leather during a pickling stage of a leather-tanning process.

4. The composition of claim 1, wherein said composition is a chrome-tanning liquor to be applied to leather during a chrome-tanning stage of a leather-tanning process.

5. The composition of claim 1, wherein said composition is a vegetable-tanning liquor to be applied to leather during a vegetable-tanning stage of a leather-tanning process.

6. The composition of claim 1, wherein said composition is a post-tan washing liquor to be applied to leather during a post-tan washing stage of a leather-tanning process.

7. The composition of claim 1, wherein said composition is a fatliquor to be applied to leather during a fatliquoring stage of a leather-tanning process.

8. The composition of claim 1, wherein the thiophanate compound is a compound of the formula:

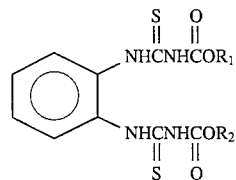

wherein $R^1$ and $R^2$ are the same or different and are a $C_1$–$C_6$

9. The composition of claim 8, wherein $R^1$ and $R^2$ are ethyl or methyl.

10. The composition of claim 1, wherein the weight ratio of the 2-(thiocyanomethylthio)benzothiazole to the thiophanate compound ranges from 99:1 to 1:99.

11. The composition of claim 10, wherein the weight ratio of the 2-(thiocyanomethylthio)benzothiazole to the thiophanate compound ranges from 60:40 to 20:80.

12. The composition of claim 11, wherein the weight ratio of the 2-(thiocyanomethylthio)benzothiazole to the thiophanate compound ranges from 50:50 to 30:70.

13. A method of protecting leather during a leather tanning process comprising the step of contacting the leather to be tanned with a leather-tanning liquor composition comprising:

(a) 2-(Thiocyanomethylthio)benzothiazole and (b) a thiophanate compound wherein (a) and (b) are present in a combined amount synergistically effective to control growth of at least one fungus on the leather.

14. The method of claim 13, wherein the thiophanate compound is thiophanate-methyl.

15. The method of claim 13, wherein said leather-tanning process comprises at least one of a pickling stage, a chrome-tanning stage, a vegetable-tanning stage, a post-tan washing stage, and a fatliquoring stage.

16. The method of claim 15, wherein said leather-tanning liquor composition is a pickling liquor, and wherein said leather to be tanned is contacted with said pickling liquor during the pickling stage of said leather tanning process.

17. The method of claim 15, wherein said leather-tanning liquor composition is a chrome-tanning liquor, and wherein said leather to be tanned is contacted with said chrome-tanning liquor during the chrome-tanning stage of said leather tanning process.

18. The method of claim 15, wherein said leather-tanning liquor composition is a vegetable-tanning liquor, and wherein said leather to be tanned is contacted with said vegetable-tanning liquor during the vegetable-tanning stage of said leather tanning process.

19. The method of claim 15, wherein said leather-tanning liquor composition is a post-tan washing liquor, and wherein said leather to be tanned is contacted with said post-tan washing liquor during the post-tan washing stage of said leather tanning process.

20. The method of claim 15, wherein said leather-tanning liquor composition is a fatliquor, and wherein said leather to be tanned is contacted with said fatliquor during the fatliquoring stage of said leather tanning process.

* * * * *

UNITED STATES PATENT AND TRADEMARK OFFICE
CERTIFICATE OF CORRECTION

PATENT NO. : 5,571,443
DATED : November 5, 1996
INVENTOR(S) : DALTON, et al.

It is certified that error appears in the above-indentified patent and that said Letters Patent is hereby corrected as shown below:

In claim 8, col. 8, in the formula, between lines 54 and 60,

"$R_1$" should read --$R^1$-- and "$R_2$" should read --$R^2$--.

Line 62, after "$C_1$-$C_6$", insert --alkyl group--.

Signed and Sealed this

Eleventh Day of March, 1997

Attest:

BRUCE LEHMAN

*Attesting Officer*   *Commissioner of Patents and Trademarks*